US011459618B2

(12) United States Patent
Mao et al.

(10) Patent No.: US 11,459,618 B2
(45) Date of Patent: Oct. 4, 2022

(54) SYSTEM AND METHOD FOR DETERMINING CETUXIMAB SENSITIVITY ON GASTRIC CANCER

(71) Applicant: CROWN BIOSCIENCE, INC. (TAICANG), Jiangsu (CN)

(72) Inventors: Binchen Mao, Jiangsu (CN); Sheng Guo, Jiangsu (CN); Henry Qixiang Li, Oceanside, CA (US)

(73) Assignee: CROWN BIOSCIENCE, INC. (TAICANG), Jiangsu (CN)

( * ) Notice: Subject to any disclaimer, the term of this patent is extended or adjusted under 35 U.S.C. 154(b) by 0 days.

(21) Appl. No.: 16/499,275

(22) PCT Filed: Mar. 28, 2018

(86) PCT No.: PCT/CN2018/080890
§ 371 (c)(1),
(2) Date: Sep. 29, 2019

(87) PCT Pub. No.: WO2018/177325
PCT Pub. Date: Oct. 4, 2018

(65) Prior Publication Data
US 2020/0071769 A1 Mar. 5, 2020

(51) Int. Cl.
*C12Q 1/68* (2018.01)
*C12Q 1/6886* (2018.01)
*G16B 40/00* (2019.01)
*G16B 40/20* (2019.01)
*G16B 50/50* (2019.01)

(52) U.S. Cl.
CPC ........... *C12Q 1/6886* (2013.01); *G16B 40/00* (2019.02); *C12Q 2600/106* (2013.01); *C12Q 2600/158* (2013.01); *G16B 40/20* (2019.02); *G16B 50/50* (2019.02)

(58) Field of Classification Search
None
See application file for complete search history.

(56) References Cited

U.S. PATENT DOCUMENTS

| | | | | |
|---|---|---|---|---|
| 10,442,862 | B2 * | 10/2019 | Yang | A61K 39/39558 |
| 2015/0152474 | A1 * | 6/2015 | Pawlowski | C07K 16/30 506/4 |
| 2015/0168411 | A1 | 6/2015 | Li et al. | |
| 2016/0017431 | A1 * | 1/2016 | Giannikopoulos | A61K 31/5377 435/7.1 |
| 2016/0040244 | A1 | 2/2016 | An et al. | |
| 2017/0119807 | A1 * | 5/2017 | Lee | A61K 31/337 |
| 2020/0260697 | A1 * | 8/2020 | Guo | C07K 16/2863 |

FOREIGN PATENT DOCUMENTS

| | | |
|---|---|---|
| CN | 101946007 A | 1/2011 |
| CN | 102459638 A | 5/2012 |
| CN | 105188742 A | 12/2015 |
| WO | 2010145796 A2 | 12/2010 |
| WO | 2014028222 A1 | 2/2014 |
| WO | 2014153018 A1 | 9/2014 |

OTHER PUBLICATIONS

Pentheroudakis et al. Biomarkers of benefit from cetuximab-based therapy in metastatic colorectal cancer: interaction of EGFR ligand expression with RAS/RAF,PIK3CA genotypes. BMC Cancer; 2013; 13: 49: p. 1-12. (Year: 2013).*
Zhang et al. A subset of gastric cancers with EGFR amplification and overexpression respond to cetuximab therapy. Scientific Reports; 2013; 3: 2992: p. 1-6. (Year: 2013).*
Stein et al. Targeting Epithelial Growth Factor Receptor (EGFR) With Cetuximab in Combination With Irinotecan as Salvage Treatment in Refractory Gastric Cancer Patients: A Retrospective Analysis and Review of the Literature. EJCMO; 2012; 4; 1: 11-17. (Year: 2012).*
Li et al. Computational approaches for microRNA studies: a review. Mamm Genome; 2010; 21:1-12. (Year: 2010).*
Leung et al. Machine Learning in Genomic Medicine: A Review of Computational Problems and Data Sets. Proceedings of the IEEE ; 2016; 104; No. 1: p. 176-197. (Year: 2016).*
D'Angelo et al. Microarray analysis in gastric cancer: A review. World J Gastroenterol. 2014; 20 (34): 11972-11976. (Year: 2014).*
Wang et al. Whole-genome sequencing and comprehensive molecular profiling identify new driver mutations in gastric cancer. Nature Genetics; 2014; 46: 573-582. (Year: 2014).*
Baselga. The EGFR as a target for anticancer therapy—focus on cetuximab. European Journal of Cancer; 2001; 37: S16-S22. (Year: 2001).*
Zhang et al. Scientific Reports; 2013; 3: 2992: p. 1-6 . (Year: 2013).*
Martinex-Ramirez et al. Journal of Cellular Biochemistry; 2016 117:1016-1026. (Year: 2016).*
Artemov et al. bioRxivpreprintdoi: https://doi.org/10.1101/095653, Dec. 2016: p. 1-21. (Year: 2016).*
Wei-Hua Li et al: "P2Y2 receptor and EGFR cooperate to promote prostate cancer cell invasion via ERK1/2 pathway", Plos one, vol. 10, No. 7., Jul. 16, 2015(Jul. 16, 2015), p. e0133165, XP055744944, DOI: 10.1371/journal.pone.0133165. p. 12-p. 13, abstract, figure 8.
Denis Joachim Irmer: "Molecular analyses of resistance and sensitivity mechanisms to anti-EGFR directed tumor therapy", Jan. 1, 2008 (Jan. 1, 2008), XP055744952, Retrieved from the Internet: URL: https://edoc.ub.uni-muenchen.de/8209/1/Irmer_Denis_Joachim.pdf[retrieved on Oct. 28, 2020], pp. 46, 108.

(Continued)

*Primary Examiner* — Jeanine A Goldberg
*Assistant Examiner* — Wahwah T Johnson
(74) *Attorney, Agent, or Firm* — Jun He Law Offices P.C.; James J. Zhu

(57) ABSTRACT

A panel of gene expression markers for gastric cancer patient treated or to be treated by cetuximab is provided. Methods and compositions are also provided, e.g., kits, for evaluating gene expression levels of the markers and methods of using such gene expression levels to predict a gastric cancer patient's response to cetuximab.

5 Claims, 4 Drawing Sheets

(56) References Cited

OTHER PUBLICATIONS

The extended European search report of European application No. 18775462.7, dated Nov. 6, 2020.
Zhang, L. et al., "A subset of gastric cancers with EGFR amplification and overexpression respond to cetuximab therapy", Scientific Reports (2013), vol. 3: 2992, pp. 1-6.
Wang, Z. et al., "RNA-Seq: a revolutionary tool for transcriptomics", Nature Reviews Genetics (Jan. 2009), vol. 10 (1), pp. 57-63(1-16).
Maher, C. A. et al., "Transcriptome sequencing to detect gene fusions in cancer", Nature (Mar. 2009), vol. 458 (7234), pp. 97-101(1-19).
Kukurba, K. R. et al., "RNA Sequencing and Analysis", Cold Spring Harbor protocols (2015), vol. 2015(11), pp. 951-969(1-29).
Gibson, U. E. M. et al., "A novel method for real time quantitative RT-PCR", Genome Research (1996), vol. 6, pp. 995-1001.
Degraves, F. J. et al., "High-sensitivity quantitative PCR platform", BioTechniques (Jan. 2003), vol. 34(1), pp. 106-115.
Deiman, B. et al., "Characteristics and Applications of Nucleic Acid Sequence-Based Amplification (NASBA)", Molecular Biotechnology (2002), vol. 20, pp. 163-179.
Barany, F. et al., "Genetic disease detection and DNA amplification using cloned thermostable ligase", Proceedings of the National Academy of Sciences (Jan. 1991), vol. 88, pp. 189-193.
Guatelli, J. C. et al., "Isothermal, in vitro amplification of nucleic acids by a multienzyme reaction modeled after retroviral replication", Proceedings of the National Academy of Sciences (Mar. 1990), vol. 87, pp. 1874-1878.
Kwoh, D. Y. et al., "Transcription-based amplification system and detection of amplified human immunodeficiency virus type 1 with a bead-based sandwich hybridization format", Proceedings of the National Academy of Sciences (Feb. 1989), vol. 86, pp. 1173-1177.
Lizardi, P. M. et al., "Exponential Amplification of Recombinant—RNA Hybridization Probes", Bio/Technology (Oct. 1988), vol. 6, pp. 1197-1202.
Holland, P. M. et al., "Detection of specific polymerase chain reaction product by utilizing the 5'-3' exonuclease activity of Thermus aquaticus DNA polymerase", Proceedings of the National Academy of Sciences (Aug. 1991), vol. 88, pp. 7276-7280.
Lee, L. G. et al., "Allelic discrimination by nick-translation PCR with fluorgenic probes", Nucleic Acids Research (1993), vol. 21(16), pp. 3761-3766.
Tyagi, S. et al., "Molecular Beacons: Probes that Fluoresce upon Hybridization", Nature Biotechnology (Mar. 1996), vol. 14, pp. 303-308.
Whitcombe, D. et al., "Detection of PCR products using self-probing amplicons and fluorescence", Nature Biotechnology (Aug. 1999), vol. 17, pp. 804-807.
Nazarenko, I. A. et al., "A closed tube format for amplification and detection of DNA based on energy transfer", Nucleic Acids Research (1997), vol. 25(12), pp. 2516-2521.
Beaucage, S. L. et al., "Deoxynucleoside phosphoramidites—A new class of key intermediates for deoxypolynucleotide synthesis", Tetrahedron Letters (1981), vol. 22(20), pp. 1859-1862.
Needham-Vandevanter, D. R. et al., "Characterization of an adduct between CC-1065 and a defined oligodeoxynucleotide duplex", Nucleic Acids Research (1984), vol. 12(15), pp. 6159-6168.
Köhler, G et al., "Continuous cultures of fused cells secreting antibody of predefined specificity", Nature (Aug. 1975), vol. 256, pp. 495-497.
Huse, W. D. et al., "Generation of a large combinatorial library of the immunoglobulin repertoire in phage lambda", Science (Dec. 1989), vol. 246, pp. 1275-1281.
Ward, E. S. et al., "Binding activities of a repertoire of single immunoglobulin variable domains secreted from *Escherichia coli*", Nature (Oct. 1989), vol. 341(6242), pp. 544-546.
Zhou, H. et al., "Regularization and variable selection via the elastic net", Journal of the Royal Statistical Society Series B(2005), vol. 67(2), pp. 301-320.
Breiman, L., "Random Forests", Machine Learning (2001), vol. 45, pp. 5-32.
Friedman, J. H., "Greedy function approximation: A gradient boosting machine", The Annals of Statistics (2001), vol. 29(5), pp. 1189-1232.
Zammatteo, N. et al., "New chips for molecular biology and diagnostics", Biotechnology Annual Review (2002), pp. 35-101.
Sosnowski, R. et al., "Active microelectronic array system for DNA hybridization, genotyping and pharmacogenomic applications", Psychiatric Genetics (2002), vol. 12(4), pp. 181-192.
Heller, M. J. et al., "DNA Microarray Technology: Devices, Systems, and Applications", Annual Review of Biomedical Engineering (2002), vol. 4, pp. 129-153.
Kolchinsky, A et al., "Analysis of SNPs and other genomic variations using gel-based chips", Human Mutation (2002), vol. 19, pp. 343-360.
McGall, G. H. et al., "High-density genechip oligonucleotide probe arrays", Advances in biochemical engineering/biotechnology (2002), vol. 77, pp. 21-42.
International Search Report of PCT Application No. PCT/CN2018/080890, dated Jun. 21, 2018.
Lieto, E. et al., "Expression of Vascular Endothelial Growth Factor (VEGF) and Epidermal Growth Factor Receptor (EGFR) is an Independent Prognostic Indicator of Worse Outcome in Gastric Cancer Patients", Annals of Surgical Oncology, vol. 15, No. 1, Sep. 2007 (Sep. 26, 2007), pp. 69-79.
Bang, Y.-J. et al., "Trastuzumab in combination with chemotherapy versus chemotherapy alone for treatment of HER2-positive advanced gastric or gastro-oesophageal junction cancer (ToGA): a phase 3, open-label, randomised controlled trial", The Lancet, vol. 376, Aug. 20, 2010 (Aug. 20, 2010), pp. 687-697.
Human Genome U219 Array Plate—Support Materials, Current NetAffx Annotation Files, HG-U219 Annotations, CSV format, Release 36 (38 MB, Apr. 13, 2016), HG-U219-na36-annot-csv.zip, Apr. 13, 2016, [retrieved on Nov. 17, 2021],Retrieved from the Internet:<http://www.affymetrix.com/support/technical/by product.affx?product=HG-U219>.
Zhang, Lianhai et al., "A subset of gastric cancers with EGFR amplification and overexpression respond to cetuximab therapy", Scientific Reports, 2013, vol. 3:2992, pp. 1-6.
Notice of Reasons for Rejection of the corresponding JP application 2019-553453.
The 1st office action and search report for the corresponding Taiwan Patent Application No. 107110723 dated May 5, 2022.

\* cited by examiner

SYSTEM AND METHOD FOR DETERMINING CETUXIMAB SENSITIVITY ON GASTRIC CANCER

CROSS-REFERENCE TO RELATED APPLICATIONS

The present application is a national phase of international application PCT/CN2018/080890, filed Mar. 28, 2018, which claims the priority of International Applications PCT/CN2017/078549, filed Mar. 29, 2017, the disclosure of which is incorporated herein by reference in the entirety.

FIELD OF THE INVENTION

The present invention generally relates to cancer treatment.

BACKGROUND

Clinical responses to anticancer therapies are often restricted to a subset of patients. To maximize the efficiency of anticancer therapy, personalized chemotherapy based on molecular biomarkers has been proposed. However, the identification of predicative biomarkers capable of predicting response to cancer chemotherapy still remains a challenge.

Gastric carcinoma is one of the most common epithelial malignancies worldwide. Although our understanding of this disease has improved during the past decade, the prognosis for patients with advanced gastric cancer remains poor: the 5-year survival rate for patients with localized disease is approximately 60%, whereas for those with distant metastasis the 5-year survival rate is only 2%.

Gene amplification and/or protein overexpression of epidermal growth factor receptor (EGFR) have been observed in a variety of solid tumors, including lung, colorectal, urinary bladder, breast, head, neck, esophageal and gastric carcinomas. In some tumors such as non-small cell lung carcinoma and colorectal carcinoma, increased EGFR expression is associated with advanced stage and an unfavorable prognosis. The EGFR gene, also called ERBB, encodes a 170-kDa transmembrane tyrosine kinase receptor, which is a member of the EGFR family. The EGFR is activated by binding to its ligands such as epidermal growth factor or transforming growth factor-alpha, resulting in homodimerization or heterodimerization with another member of the EGFR family. This receptor activation is followed by phosphorylation of specific tyrosine residues within the cytoplasmic tail, stimulating the downstream signaling pathway that regulates cell proliferation, migration, adhesion, differentiation and survival.

Cetuximab is a recombinant human/mouse chimeric monoclonal antibody against EGFR. Cetuximab has been approved for treating EGFR-expressing metastatic colorectal cancer (mCRC) without activating KRAS mutation, and squamous cell carcinoma of the head and neck (SCCHN), but yet for gastric cancer.

A preclinical trial identified 4 of 20 (20%) gastric cancer patient-derived xenografts with EGFR amplification and overexpression responded to cetuximab treatment (Zhang L H et al., A subset of gastric cancers with EGFR amplification and overexpression respond to cetuximab therapy, *Scientific Reports* (2013) 3:2992). However, EGFR as a single gene biomarker could fail under at least two scenarios: the expression level of EGFR is within the medium range or EGFR gene carries a deleterious mutation. Therefore, there is need to identify additional biomarkers to complement with EGFR expression to accurately predict the response to cetuximab in gastric cancer patients.

SUMMARY OF INVENTION

In one aspect, the present disclosure provides a method for predicting cetuximab sensitivity in a patient having gastric cancer. In one embodiment, the method comprising: measuring the levels of RNA expression of two or more biomarkers comprising EGFR and a second biomarker in a tumor sample from the patient, wherein the second biomarkers is SDC2, P2RY2 or MAP6D1; comparing each of the detected levels of RNA expression of the two or more biomarkers to a corresponding predetermined reference level; and determining a likelihood of the patient being responsive to cetuximab.

In certain embodiments, the levels of RNA expression are measured by an amplification assay, a hybridization assay, a sequencing assay or an array.

In one embodiment, the comparing step of the method is performed by a processor of a computing device.

In one embodiment, the determining step of the method is performed by a processor of a computing device.

In one embodiment, the determining step comprises using a machine learning model. In one embodiment, the machine learning model is a support vector machine model.

In one embodiment, the method described herein further comprises recommending the administration of cetuximab to the patient.

Also provided herein is a kit for detecting the level of RNA expression of two or more biomarkers comprising EGFR and a second biomarker. In one embodiment, the second biomarkers is SDC2, P2RY2 or MAP6D1.

The present disclosure also provides a microarray including probes for detecting the level of RNA expression of two or more biomarkers. In one embodiment, the two or more biomarkers is SDC2, P2RY2 or MAP6D1.

In another aspect, the present disclosure provides a non-transitory computer readable medium having instructions stored thereon. In one embodiment, the instructions, when executed by a processor, cause the processor to: retrieve levels of RNA expression of two or more biomarkers comprising EGFR and a second biomarker, wherein the levels are obtained from a tumor sample from a patient having gastric cancer, and wherein the second biomarker is SDC2, P2RY2 or MAP6D1; comparing each of the levels of RNA expression of the two or more biomarkers to a corresponding predetermined reference level; and determining a likelihood of the patient being responsive to cetuximab.

In yet another aspect, the present disclosure provides a system predicting cetuximab sensitivity in a patient having gastric cancer. In one embodiment, the system comprises: an in vitro diagnostic kit comprising primers for detecting the level of RNA expression of two or more biomarkers comprising EGFR and a second biomarker selected from SDC2, P2RY2 and MAP6D1; and a non-transitory computer readable medium having instructions stored thereon. In one embodiment, the instructions, when executed by a processor, cause the processor to: retrieve the levels of RNA expression of the two or more biomarkers detected using the in vitro diagnostic kit, compare each of the levels of RNA expression of the two or more biomarkers to a corresponding predetermined reference level, and determine a likelihood of the patient being responsive to cetuximab.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

DETAILED DESCRIPTION OF THE INVENTION

Figure 1:
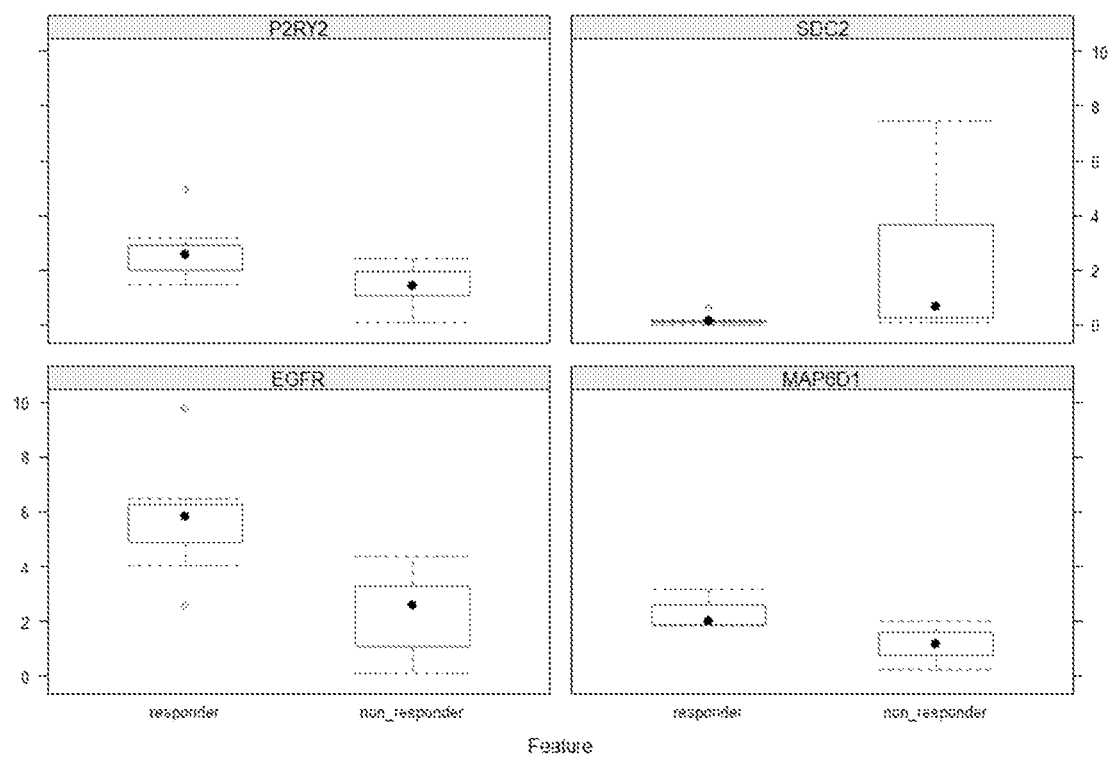
FIG. 1 shows the gene expression level distribution against response to cetuximab treatment.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Definitions

The following definitions are provided to assist the reader. Unless otherwise defined, all terms of art, notations and other scientific or medical terms or terminology used herein are intended to have the meanings commonly understood by those of skill in the chemical and medical arts. In some cases, terms with commonly understood meanings are defined herein for clarity and/or for ready reference, and the inclusion of such definitions herein should not necessarily be construed to represent a substantial difference over the definition of the term as generally understood in the art.

As used herein, the singular forms "a", "an" and "the" include plural references unless the context clearly dictates otherwise.

The term "amount" or "level" refers to the quantity of a polynucleotide of interest or a polypeptide of interest present in a sample. Such quantity may be expressed in the absolute terms, i.e., the total quantity of the polynucleotide or polypeptide in the sample, or in the relative terms, i.e., the concentration of the polynucleotide or polypeptide in the sample.

As used herein, the term "cancer" refers to any diseases involving an abnormal cell growth and include all stages and all forms of the disease that affects any tissue, organ or cell in the body. The term includes all known cancers and neoplastic conditions, whether characterized as malignant, benign, soft tissue, or solid, and cancers of all stages and grades including pre- and post-metastatic cancers. In general, cancers can be categorized according to the tissue or organ from which the cancer is located or originated and morphology of cancerous tissues and cells. As used herein, cancer types include, without limitation, acute lymphoblastic leukemia (ALL), acute myeloid leukemia, adrenocortical carcinoma, anal cancer, astrocytoma, childhood cerebellar or cerebral, basal-cell carcinoma, bile duct cancer, bladder cancer, bone tumor, brain cancer, cerebellar astrocytoma, cerebral astrocytoma/malignant glioma, ependymoma, medulloblastoma, supratentorial primitive neuroectodermal tumors, visual pathway and hypothalamic glioma, breast cancer, Burkitt's lymphoma, ervical cancer, chronic lymphocytic leukemia, chronic myelogenous leukemia, colon cancer, emphysema, endometrial cancer, ependymoma, esophageal cancer, Ewing's sarcoma, retinoblastoma, gastric (stomach) cancer, glioma, head and neck cancer, heart cancer, Hodgkin lymphoma, islet cell carcinoma (endocrine pancreas), Kaposi sarcoma, kidney cancer (renal cell cancer), laryngeal cancer, leukaemia, liver cancer, lung cancer, neuroblastoma, non-Hodgkin lymphoma, ovarian cancer, pancreatic cancer, pharyngeal cancer, prostate cancer, rectal cancer, renal cell carcinoma (kidney cancer), retinoblastoma, Ewing family of tumors, skin cancer, stomach cancer, testicular cancer, throat cancer, thyroid cancer, vaginal cancer.

It is noted that in this disclosure, terms such as "comprises", "comprised", "comprising", "contains", "containing" and the like have the meaning attributed in United States Patent law; they are inclusive or open-ended and do not exclude additional, un-recited elements or method steps. Terms such as "consisting essentially of" and "consists essentially of" have the meaning attributed in United States Patent law; they allow for the inclusion of additional ingredients or steps that do not materially affect the basic and novel characteristics of the claimed invention. The terms "consists of" and "consisting of" have the meaning ascribed to them in United States Patent law; namely that these terms are close ended.

A "cell", as used herein, can be prokaryotic or eukaryotic. A prokaryotic cell includes, for example, bacteria. A eukaryotic cell includes, for example, a fungus, a plant cell, and an animal cell. The types of an animal cell (e.g., a mammalian cell or a human cell) includes, for example, a cell from circulatory/immune system or organ (e.g., a B cell, a T cell (cytotoxic T cell, natural killer T cell, regulatory T cell, T helper cell), a natural killer cell, a granulocyte (e.g., basophil granulocyte, an eosinophil granulocyte, a neutrophil granulocyte and a hypersegmented neutrophil), a monocyte or macrophage, a red blood cell (e.g., reticulocyte), a mast cell, a thrombocyte or megakaryocyte, and a dendritic cell); a cell from an endocrine system or organ (e.g., a thyroid cell (e.g., thyroid epithelial cell, parafollicular cell), a parathyroid cell (e.g., parathyroid chief cell, oxyphil cell), an adrenal cell (e.g., chromaffin cell), and a pineal cell (e.g., pinealocyte)); a cell from a nervous system or organ (e.g., a glioblast (e.g., astrocyte and oligodendrocyte), a microglia, a magnocellular neurosecretory cell, a stellate cell, a boettcher cell, and a pituitary cell (e.g., gonadotrope, corticotrope, thyrotrope, somatotrope, and lactotroph)); a cell from a respiratory system or organ (e.g., a pneumocyte (a type I pneumocyte and a type II pneumocyte), a clara cell, a goblet cell, an alveolar macrophage); a cell from circular system or organ (e.g., myocardiocyte and pericyte); a cell from digestive system or organ (e.g., a gastric chief cell, a parietal cell, a goblet cell, a paneth cell, a G cell, a D cell, an ECL cell, an I cell, a K cell, an S cell, an enteroendocrine cell, an enterochromaffin cell, an APUD cell, a liver cell (e.g., a hepatocyte and Kupffer cell)); a cell from integumentary system or organ (e.g., a bone cell (e.g., an osteoblast, an osteocyte, and an osteoclast), a teeth cell (e.g., a cementoblast, and an ameloblast), a cartilage cell (e.g., a chondroblast and a chondrocyte), a skin/hair cell (e.g., a trichocyte, a keratinocyte, and a melanocyte (Nevus cell)), a muscle cell (e.g., myocyte), an adipocyte, a fibroblast, and a tendon cell), a cell from urinary system or organ (e.g., a podocyte, a juxtaglomerular cell, an intraglomerular mesangial cell, an extraglomerular mesangial cell, a kidney proximal tubule brush border cell, and a macula densa cell), and a cell from reproductive system or organ (e.g., a spermatozoon, a Sertoli cell, a leydig cell, an ovum, an oocyte). A cell can be normal, healthy cell; or a diseased or unhealthy cell (e.g., a cancer cell). A cell further includes a mammalian zygote or a stem cell which include an embryonic stem cell, a fetal stem cell, an induced pluripotent stem cell, and an adult stem cell. A stem cell is a cell that is capable of undergoing cycles of cell division while maintaining an undifferentiated state and differentiating into specialized cell types. A stem cell can be an omnipotent stem cell, a pluripotent stem cell, a multipotent stem cell, an oligopotent stem cell and a unipotent stem cell, any of which may be induced from a somatic cell. A stem cell may also include a cancer stem cell. A mammalian cell can be a rodent cell, e.g., a mouse, rat, hamster cell. A mammalian cell can be a lagomorpha cell, e.g., a rabbit cell. A mammalian cell can also be a primate cell, e.g., a human cell. In certain examples, the cells are those used for mass bioproduction, e.g., CHO cells.

The term "complementarity" refers to the ability of a nucleic acid to form hydrogen bond(s) with another nucleic acid sequence by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%>, 70%>, 80%>, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%. 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

The terms "determining," "assessing," "assaying," "measuring" and "detecting" can be used interchangeably and refer to both quantitative and semi-quantitative determinations. Where either a quantitative and semi-quantitative determination is intended, the phrase "determining a level" of a polynucleotide or polypeptide of interest or "detecting" a polynucleotide or polypeptide of interest can be used.

The term "gene product" or "gene expression product" refers to an RNA or protein encoded by the gene.

The term "hybridizing" refers to the binding, duplexing, or hybridizing of a nucleic acid molecule preferentially to a particular nucleotide sequence under stringent conditions. The term "stringent conditions" refers to conditions under which a probe will hybridize preferentially to its target subsequence, and to a lesser extent to, or not at all to, other sequences in a mixed population (e.g., a cell lysate or DNA preparation from a tissue biopsy). A "stringent hybridization" and "stringent hybridization wash conditions" in the context of nucleic acid hybridization (e.g., as in array, microarray, Southern or northern hybridizations) are sequence dependent, and are different under different environmental parameters. An extensive guide to the hybridization of nucleic acids is found in, e.g., Tijssen *Laboratory Techniques in Biochemistry and Molecular Bio logy—Hybridization with Nucleic Acid Probes* part I, Ch. 2, "Overview of principles of hybridization and the strategy of nucleic acid probe assays," (1993) Elsevier, N.Y. Generally, highly stringent hybridization and wash conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Very stringent conditions are selected to be equal to the Tm for a particular probe. An example of stringent hybridization conditions for hybridization of complementary nucleic acids which have more than 100 complementary residues on an array or on a filter in a Southern or northern blot is 42° C. using standard hybridization solutions (see, e.g., Sambrook and Russell *Molecular Cloning: A Laboratory Manual* (3rd ed.) Vol. 1-3 (2001) Cold Spring Harbor Laboratory, Cold Spring Harbor Press, NY). An example of highly stringent wash conditions is 0.15 M NaCl at 72° C. for about 15 minutes. An example of stringent wash conditions is a 0.2×SSC wash at 65° C. for 15 minutes. Often, a high stringency wash is preceded by a low stringency wash to remove background probe signal. An example medium stringency wash for a duplex of, e.g., more than 100 nucleotides, is 1×SSC at 45° C. for 15 minutes. An example of a low stringency wash for a duplex of, e.g., more than 100 nucleotides, is 4×SSC to 6×SSC at 40° C. for 15 minutes.

The term "nucleic acid" and "polynucleotide" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, shRNA, single-stranded short or long RNAs, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

The term "overall survival" refers to the time interval from either the time of diagnosis or the start of treatment that the patient is still alive.

The term "prognose" or "prognosing" as used herein refers to the prediction or forecast of the future course or outcome of a disease or condition.

The term "progression-free survival" refers to the time interval from treatment of the patient until the progression of cancer or death of the patient, whichever occurs first.

In general, a "protein" is a polypeptide (i.e., a string of at least two amino acids linked to one another by peptide bonds). Proteins may include moieties other than amino acids (e.g., may be glycoproteins) and/or may be otherwise processed or modified. Those of ordinary skill in the art will appreciate that a "protein" can be a complete polypeptide chain as produced by a cell (with or without a signal sequence), or can be a functional portion thereof. Those of ordinary skill will further appreciate that a protein can sometimes include more than one polypeptide chain, for example linked by one or more disulfide bonds or associated by other means.

The term "recommending" or "suggesting" in the context of a treatment of a disease, refers to making a suggestion or a recommendation for therapeutic intervention (e.g., drug therapy, adjunctive therapy, etc.) and/or disease management which are specifically applicable to the patient.

The terms "responsive," "clinical response," "positive clinical response," and the like, as used in the context of a patient's response to a cancer therapy, are used interchangeably and refer to a favorable patient response to a treatment as opposed to unfavorable responses, i.e. adverse events. In a patient, beneficial response can be expressed in terms of a number of clinical parameters, including loss of detectable tumor (complete response, CR), decrease in tumor size and/or cancer cell number (partial response, PR), tumor growth arrest (stable disease, SD), enhancement of anti-tumor immune response, possibly resulting in regression or rejection of the tumor; relief, to some extent, of one or more symptoms associated with the tumor; increase in the length of survival following treatment; and/or decreased mortality at a given point of time following treatment. Continued increase in tumor size and/or cancer cell number and/or tumor metastasis is indicative of lack of beneficial response to treatment. In a population the clinical benefit of a drug, i.e., its efficacy can be evaluated on the basis of one or more endpoints. For example, analysis of overall response rate (ORR) classifies as responders those patients who experience CR or PR after treatment with drug. Analysis of disease control (DC) classifies as responders those patients who experience CR, PR or SD after treatment with drug. A positive clinical response can be assessed using any endpoint indicating a benefit to the patient, including, without limitation, (1) inhibition, to some extent, of tumor growth, including slowing down and complete growth arrest; (2) reduction in the number of tumor cells; (3) reduction in tumor size; (4) inhibition (i.e., reduction, slowing down or complete stopping) of tumor cell infiltration into adjacent peripheral organs and/or tissues; (5) inhibition of metastasis; (6) enhancement of anti-tumor immune response, possibly resulting in regression or rejection of the tumor; (7) relief, to some extent, of one or more symptoms associated with the tumor; (8) increase in the length of survival following treatment; and/or (9) decreased mortality at a given point of time following treatment. Positive clinical response may also be expressed in terms of various measures of clinical outcome. Positive clinical outcome can also be considered in the context of an individual's outcome relative to an outcome of a population of patients having a comparable clinical diagnosis, and can be assessed using various endpoints such as an increase in the duration of recurrence-free interval (RFI), an increase in the time of survival as compared to overall survival (OS) in a population, an increase in the time of disease-free survival (DFS), an increase in the duration of distant recurrence-free interval (DRFI), and the like. Additional endpoints include a likelihood of any event (AE)-free survival, a likelihood of metastatic relapse (MR)-free survival (MRFS), a likelihood of disease-free survival (DFS), a likelihood of relapse-free survival (RFS), a likelihood of first progression (FP), and a likelihood of distant metastasis-free survival (DMFS). An increase in the likelihood of positive clinical response corresponds to a decrease in the likelihood of cancer recurrence or relapse.

The term "standard control" as used herein refers to a predetermined amount or concentration of a polynucleotide sequence or polypeptide sequence that is present in an established normal tissue sample, e.g., a healthy, non-cancer tissue sample, or a diploid, non-transformed, non-cancerous, genomically stable healthy human cell line. The standard control value is suitable for the use of a method of the present invention, to serve as a basis for comparing the amount of a specific mRNA or protein that is present in a test sample. An established sample serving as a standard control provides an average amount of a specific mRNA or protein that is typical in a normal tissue sample. A standard control value may vary depending on the nature of the sample as well as other factors such as the gender, age, ethnicity of the subjects based on whom such a control value is established.

As used herein, the term "subject" refers to a human or any non-human animal (e.g., mouse, rat, rabbit, dog, cat, cattle, swine, sheep, horse or primate). A human includes pre and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

The term "tumor sample" includes a biological sample or a sample from a biological source that contains one or more tumor cells. Biological samples include samples from body fluids, e.g., blood, plasma, serum, or urine, or samples derived, e.g., by biopsy, from cells, tissues or organs, preferably tumor tissue suspected to include or essentially consist of cancer cells.

The term "treatment," "treat," or "treating" refer to a method of reducing the effects of a cancer (e.g., breast cancer, lung cancer, ovarian cancer or the like) or symptom of cancer. Thus, in the disclosed method, treatment can refer to a 10%, 20%, 30%, 40%, 50%, 60%, 70%), 80%), 90%), or 100% reduction in the severity of a cancer or symptom of the cancer. For example, a method of treating a disease is considered to be a treatment if there is a 10% reduction in one or more symptoms of the disease in a subject as compared to a control. Thus, the reduction can be a 10%, 20%, 30%, 40%, 50%, 60%, 70%, 80%, 90%, 100% or any percent reduction between 10 and 100% as compared to native or control levels. It is understood that treatment does not necessarily refer to a cure or complete ablation of the disease, condition, or symptoms of the disease or condition.

Biomarkers for Predicting Response to Cetuximab

The methods and compositions described herein are based, in part, on the discovery of a panel of biomarkers whose expression is correlated with cetuximab sensitivity in a gastric cancer patient. In one aspect, the present disclosure provides methods for predicting response to cetuximab in a patient having gastric cancer. In certain embodiments, the methods comprise: measuring the level of expression of two or more biomarkers comprising EGFR and a second biomarker in a tumor sample from the patient wherein the second biomarkers is SDC2, P2RY2 or MAP6D1; comparing each of the detected levels of expression of the two or more biomarkers to a corresponding predetermined reference level; and determining a likelihood of the patient being responsive to cetuximab. In some cases, the measurement is performed prior to the patient being treated with cetuximab.

The human epidermal growth factor receptor (EGFR) mRNA (coding) sequence is set forth in, e.g., NCBI Ref. Seq. Nos. NM_001346941.1, NM_005228.4, NM_001346898.1, NM_001346900.1, NM_001346899.1, NM_001346897.1, NM_201284.1, NM_201283.1, NM_201282.1. The human EGFR polypeptide sequence is set forth in, e.g., NCBI Ref. Seq. Nos. NP_005219.2, NP_958439.1, NP_958440.1, NP_958441.1, NP_001333826.1, NP_001333828.1, NP_001333829.1, NP_001333827.1, NP_001333870.1.

The human syndecan-2 (SDC2) mRNA (coding) sequence is set forth in, e.g., NCBI Ref. Seq. No. NM_002998.3. The human SDC2 polypeptide sequence is set forth in, e.g., NCBI Ref. Seq. No. NP_002989.2.

The human P2Y purinoceptor 2 (P2RY2) mRNA (coding) sequence is set forth in, e.g., NCBI Ref. Seq. Nos. XM_017017839.1, XM_005274019.4, XM_005274021.4, XM_005274020.4, XM_011545074.2, XR_001747890.1, XR_001747891.1, XR_001747892.1. The human P2RY2 polypeptide sequence is set forth in, e.g., NCBI Ref Seq. Nos. NP_002555.3, NP_788085.2, NP_788086.2.

The human MAP6 domain-containing protein 1 (MAP6D1) mRNA (coding) sequence is set forth in, e.g., NCBI Ref. Seq. No. NM_024871.2. The human BRCA2 polypeptide sequence is set forth in, e.g., NCBI Ref. Seq. No. NP_079147.1.

Methods of Quantifying RNA Levels

The methods of the present disclosure include measuring the level of RNA expression of at least a subset of the predicting biomarkers, e.g., a subset of at least 6 genes, at least 7 gene, at least 8 genes, at least 9 genes, at least 10 genes, at least 11 genes, at least 12 genes, at least 13 genes, at least 14 genes and at least 15 genes of the 16 genes, in a tumor sample obtained from a patient suspected of having cancer or at risk of having cancer. In some embodiments, the patient has been diagnosed with cancer.

The tumor sample can be a biological sample comprising cancer cells. In some embodiments, the tumor sample is a fresh or archived sample obtained from a tumor, e.g., by a tumor biopsy or fine needle aspirate. The sample also can be any biological fluid containing cancer cells. The tumor sample can be isolated or obtained from any number of primary tumors, including, but not limited to, tumors of the breast, lung, prostate, brain, liver, kidney, intestines, colon, spleen, pancreas, thymus, testis, ovary, uterus, and the like. In some embodiments, the tumor sample is from a tumor cell line. The collection of a tumor sample from a subject is performed in accordance with the standard protocol generally followed by hospital or clinics, such as during a biopsy.

Any method known to those of ordinary skill in the art can be used to measure RNA expression levels. In some embodiments, RNA is isolated from the tumor sample. RNA can be isolated from the tumor sample using a variety of methods. Standard methods for RNA extraction from tissue or cells are described in, for example, Ausubel et al., *Current Protocols of Molecular Biology* (1997) John Wiley & Sons, and Sambrook and Russell, *Molecular Cloning: A Laboratory Manual* 3rd ed. (2001). Commercially available kits, e.g., RNeasy® mini columns (Qiagen), PureLink® RNA mini kit (Thermo Fisher Scientific), etc. can also be used to isolate RNA.

The level of RNA (e.g., mRNA) expression of the predicting biomarkers described above can be detected or measured by a variety of methods including, but not limited to, an amplification assay, a hybridization assay, a sequencing assay, or an array. Non-limiting examples of such methods include reverse-transcription polymerase chain reaction (RT-PCR); quantitative real-time PCR (qRT-PCR); quantitative PCR, such as TaqMan®; Northern blotting; in situ hybridization assays; microarray analysis, e.g., microarrays from Nano String Technologies; multiplexed hybridization-based assays, e.g., QuantiGene 2.0 Multiplex Assay from Panomics; serial analysis of gene expression (SAGE); cDNA-mediated annealing, selection, extension, and ligation; direct sequencing or pyrosequencing; massively parallel sequencing; next generation sequencing; high performance liquid chromatography (HPLC) fragment analysis; capillarity electrophoresis; and the like. Various methods involving amplification reactions and/or reactions in which probes are linked to a solid support and used to quantify RNA may be used. Alternatively, the RNA may be linked to a solid support and quantified using a probe to the sequence of interest.

In certain embodiments, the RNA expression of the predicting biomarkers described above is measured by high throughput sequencing, e.g., whole transcriptome shotgun sequencing (RNA sequencing). The method of RNA sequencing has been described (see Wang Z, Gerstein M and Snyder M, *Nature Review Genetics* (2009) 10:57-63; Maher C A et al., *Nature* (2009) 458:97-101; Kukurba K & Montgomery SB, Cold Spring Harbor Protocols (2015) 2015(11): 951-969).

In some embodiments, the target RNA is first reverse transcribed and the resulting cDNA is quantified. In some embodiments, RT-PCR or other quantitative amplification techniques are used to quantify the target RNA. Amplification of cDNA using PCR is well known (see U.S. Pat. Nos. 4,683,195 and 4,683,202; PCR PROTOCOLS: A GUIDE TO METHODS AND APPLICATIONS (Innis et al., eds, 1990)). Methods of quantitative amplification are disclosed in, e.g., U.S. Pat. Nos. 6,180,349; 6,033,854; and 5,972,602, as well as in, e.g., Gibson et al., *Genome Research* (1996) 6:995-1001; DeGraves, et al., *Biotechniques* (2003) 34(1): 106-10, 112-5; Deiman B, et al., *Mol Biotechnol.* (2002) 20(2): 163-79. Alternative methods for determining the level of a mRNA of interest in a sample may involve other nucleic acid amplification methods such as ligase chain reaction (Barany, *Proc. Natl. Acad. Sci. USA* (1991) 88: 189-193), self-sustained sequence replication (Guatelli et al., *Proc. Natl. Acad. Sci. USA* (1990) 87:1874-1878), transcriptional amplification system (Kwoh et al., *Proc. Natl. Acad. Sci. USA* (1989) 86: 1173-1177), Q-Beta Replicase (Lizardi et al., *Biotechnology* (1988) 6: 1197), rolling circle replication (U.S. Pat. No. 5,854,033) or any other nucleic acid amplification method, followed by the detection of the amplified molecules using techniques well known to those of skill in the art.

In general, quantitative amplification is based on the monitoring of the signal (e.g., fluorescence of a probe) representing copies of the template in cycles of an amplification (e.g., PCR) reaction. One method for detection of amplification products is the 5-3' exonuclease "hydrolysis" PCR assay (also referred to as the TaqMan® assay) (U.S. Pat. Nos. 5,210,015 and 5,487,972; Holland et al., PNAS USA (1991) 88: 7276-7280; Lee et al, *Nucleic Acids Res.*

(1993) 21: 3761-3766). This assay detects the accumulation of a specific PCR product by hybridization and cleavage of a doubly labeled fluorogenic probe (the "TaqMan®" probe) during the amplification reaction. The fluorogenic probe consists of an oligonucleotide labeled with both a fluorescent reporter dye and a quencher dye. During PCR, this probe is cleaved by the 5'-exonuclease activity of DNA polymerase if, and only if, it hybridizes to the segment being amplified. Cleavage of the probe generates an increase in the fluorescence intensity of the reporter dye.

Another method of detecting amplification products that relies on the use of energy transfer is the "beacon probe" method described by Tyagi and Kramer, *Nature Biotech.* (1996) 14:303-309, which is also the subject of U.S. Pat. Nos. 5,119,801 and 5,312,728. This method employs oligonucleotide hybridization probes that can form hairpin structures. On one end of the hybridization probe (either the 5' or 3' end), there is a donor fluorophore, and on the other end, an acceptor moiety. In the case of the Tyagi and Kramer method, this acceptor moiety is a quencher, that is, the acceptor absorbs energy released by the donor, but then does not itself fluoresce. Thus, when the beacon is in the open conformation, the fluorescence of the donor fluorophore is detectable, whereas when the beacon is in hairpin (closed) conformation, the fluorescence of the donor fluorophore is quenched. When employed in PCR, the molecular beacon probe, which hybridizes to one of the strands of the PCR product, is in "open conformation," and fluorescence is detected, while those that remain unhybridized will not fluoresce (Tyagi and Kramer, *Nature Biotechnol.* (1996) 14: 303-306). As a result, the amount of fluorescence will increase as the amount of PCR product increases, and thus may be used as a measure of the progress of the PCR. Those of skill in the art will recognize that other methods of quantitative amplification are also available.

Various other techniques for performing quantitative amplification of nucleic acids are also known. For example, some methodologies employ one or more probe oligonucleotides that are structured such that a change in fluorescence is generated when the oligonucleotide(s) is hybridized to a target nucleic acid. For example, one such method involves a dual fluorophore approach that exploits fluorescence resonance energy transfer (FRET), e.g., LightCycler™ hybridization probes, where two oligo probes anneal to the amplicon. The oligonucleotides are designed to hybridize in a head-to-tail orientation with the fluorophores separated at a distance that is compatible with efficient energy transfer. Other examples of labeled oligonucleotides that are structured to emit a signal when bound to a nucleic acid or incorporated into an extension product include: Scorpions™ probes (e.g., Whitcombe et al., *Nature Biotechnology* (1999) 17:804-807, and U.S. Pat. No. 6,326,145), Sunrise™ (or Amplifluor™) probes (e.g., Nazarenko et al., *Nuc. Acids Res.* (1997) 25:2516-2521, and U.S. Pat. No. 6,117,635), and probes that form a secondary structure that results in reduced signal without a quencher and that emits increased signal when hybridized to a target (e.g., Lux Probes™).

In other embodiments, intercalating agents that produce a signal when intercalated in double stranded DNA may be used. Exemplary agents include SYBR GREEN™ and SYBR GOLD™. Since these agents are not template-specific, it is assumed that the signal is generated based on template-specific amplification. This can be confirmed by monitoring signal as a function of temperature because melting point of template sequences will generally be much higher than, for example, primer-dimers, etc.

In other embodiments, the mRNA is immobilized on a solid surface and contacted with a probe, e.g., in a dot blot or Northern format. In an alternative embodiment, the probe(s) are immobilized on a solid surface and the mRNA is contacted with the probe(s), for example, in a gene chip array. A skilled artisan can readily adapt known mRNA detection methods for use in detecting the level of mRNA encoding the biomarkers or other proteins of interest.

In some embodiments, microarrays, e.g., are employed. DNA microarrays provide one method for the simultaneous measurement of the expression levels of large numbers of genes. Each array consists of a reproducible pattern of capture probes attached to a solid support. Labeled RNA or DNA is hybridized to complementary probes on the array and then detected by laser scanning. Hybridization intensities for each probe on the array are determined and converted to a quantitative value representing relative gene expression levels. See, U.S. Pat. Nos. 6,040,138, 5,800,992 and 6,020,135, 6,033,860, and 6,344,316. High-density oligonucleotide arrays are particularly useful for determining the gene expression profile for a large number of RNA's in a sample.

Techniques for the synthesis of these arrays using mechanical synthesis methods are described in, e.g., U.S. Pat. No. 5,384,261. Although a planar array surface is often employed the array may be fabricated on a surface of virtually any shape or even a multiplicity of surfaces. Arrays may be peptides or nucleic acids on beads, gels, polymeric surfaces, fibers such as fiber optics, glass or any other appropriate substrate, see U.S. Pat. Nos. 5,770,358, 5,789, 162, 5,708,153, 6,040,193 and 5,800,992. Arrays may be packaged in such a manner as to allow for diagnostics or other manipulation of an all-inclusive device.

In some embodiments, gene-specific probes and/or primers are used in hybridization assays to detect RNA expression. The probes and/or primers may be labeled with any detectable moiety or compound, such as a radioisotope, fluorophore, chemiluminescent agent, and enzyme.

The probes and primers necessary for practicing the present invention can be synthesized and labeled using well known techniques. Oligonucleotides used as probes and primers may be chemically synthesized according to the solid phase phosphoramidite triester method first described by Beaucage and Caruthers, *Tetrahedron Letts.* (1981) 22: 1859-1862, using an automated synthesizer, as described in Needham-Van Devanter et al, Nucleic Acids Res. (1984) 12:6159-6168.

In some embodiments, the methods further comprise detecting level of expression of one or more reference genes that can be used as controls to determine expression levels. Such genes are typically expressed constitutively at a high level and can act as a reference for determining accurate gene expression level estimates. Non-limiting examples of control genes include ARPC2, ATF4, ATP5B, B2M, CDH4, CELF1, CLTA, CLTC, COPB1, CTBP1, CYC1, CYFIP1, DAZAP2, DHX15, DIMT1, EEF1A1, FLOT2, GAPDH, GUSB, HADHA, HDLBP, HMBS, HNRNPC, HPRT1, HSP90AB1, MTCH1, MYL12B, NACA, NDUFB8, PGK1, PPIA, PPIB, PTBP1, RPL13A, RPLP0, RPS13, RPS23, RPS3, S100A6, SDHA, SEC31A, SET, SF3B1, SFRS3, SNRNP200, STARD7, SUMO1, TBP, TFRC, TMBIM6, TPT1, TRA2B, TUBA1C, UBB, UBC, UBE2D2, UBE2D3, VAMP3, XPO1, YTHDC1, YWHAZ, and 18S rRNA genes. Accordingly, a determination of RNA expression levels of the genes of interest, e.g., the gene expression levels of the panel of the predicting biomarkers may also comprise determining expression levels of one or more reference genes disclosed above.

The level of mRNA expression of each of the biomarkers described herein can be normalized to a reference level for a control gene. The control value can be predetermined, determined concurrently, or determined after a sample is obtained from the subject. The standard can be run in the same assay or can be a known standard from a previous assay. In the cases when the level of RNA expression is determined by RNA sequencing, the level of RNA expression of each of the biomarkers can be normalized to the total reads of the sequencing. The normalized levels of mRNA expression of the biomarker genes can be transformed in to a score, e.g., using the methods and models described herein.

Methods of Quantifying Protein Levels

In some embodiments, the methods disclosed herein include determining the level of polypeptides encoded by at least a subset of the panel of biomarker genes. Any method known to those of ordinary skill in the art can be used to detect protein expression levels. A general overview of the applicable technology can be found in Harlow & Lane, *Antibodies: A Laboratory Manual* (1988) and Harlow & Lane, *Using Antibodies* (1999). Methods of producing polyclonal and monoclonal antibodies that react specifically with an allelic variant are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature* (1975) 256:495-497). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* (1989) 246:1275-1281; Ward et al, *Nature* (1989) 341:544-546).

The level of such polypeptides can be detected by a variety of methods including, but not limited to, Western blotting, immunoassays, e.g., enzyme-linked immunosorbent assay (ELISA), enzyme immunoassay (EIA), radioimmunoassay (RIA), sandwich assays, competitive assays, immunohistochemistry, mass spectrometry, 2-D gel electrophoresis, protein array, antibody array, and the like. For a review of immunological and immunoassay procedures, see Basic and Clinical Immunology (Stites & Terr eds., 7th ed. 1991). Moreover, the immunoassays can be performed in any of several configurations, which are reviewed extensively in Enzyme Immunoassay (Maggio, ed., 1980); and Harlow & Lane, supra. For a review of the general immunoassays, see also *Methods in Cell Biology: Antibodies in Cell Biology*, volume 37 (Asai, ed. 1993); *Basic and Clinical Immunology* (Stites & Terr, eds., 7th ed. 1991). Similar to normalizing the mRNA level of the biomarker genes, the level of protein expression can also be compared and normalized to a control value for a standard.

Methods for Predicting Response to Cetuximab

After measuring the expression level of the panel of the biomarkers, the method disclosed herein includes determining a likelihood of the patient being responsive to cetuximab. In certain embodiments, the likelihood can be determined based on models using machine learning techniques such as partial least square (Wold S et al., PLS for Multivariate Linear Modeling, *Chemometric Methods in Molecular Design* (1995) Han van de Waterbeemd (ed.), pp. 195-218. VCH, Weinheim), elastic net (Zou H et al., Regularization and Variable Selection via the Elastic Net, *Journal of the Royal Statistical Society*, Series B (2005) 67(2): 301-320), support vector machine (Vapnik V, The Nature of Statistical Learning Theory (2010) Springer), random forest (Breiman L, Random Forests, *Machine Learning* (2001) 45: 5-32), neural net (Bishop C, Neural Networks for Pattern Recognition (1995) Oxford University Press, Oxford) and gradient boosting machine (Friedman J, Greedy Function Approximation: A Gradient Boosting Machine, *Annals of Statistics* (2001) 29(5), 1189-1232). In one case, the likelihood is determined based on models using supporting vector machine.

As used herein, "machine learning" refers to a computer-implemented technique that gives computer systems the ability to progressively improve performance on a specific task with data, i.e., to learn from the data, without being explicitly programmed. Machine learning technique adopts algorithms that can learn from and make prediction on data through building a model, i.e., a description of a system using mathematical concepts, from sample inputs. A core objective of machine learning is to generalize from the experience, i.e., to perform accurately on new data after having experienced a learning data set. In the context of biomedical diagnosis or prognosis, machine learning techniques generally involves supervised learning process, in which the computer is presented with example inputs (e.g., signature of gene expression) and their desired outputs (e.g., responsiveness) to learn a general rule that maps inputs to outputs. Different models, i.e., hypothesis, can be employed in the generalization process. For the best performance in the generalization, the complexity of the hypothesis should match the complexity of the function underlying the data.

Computer-Implemented Methods, Systems and Devices

Any of the methods described herein may be totally or partially performed with a computer system including one or more processors, which can be configured to perform the steps. Thus, embodiments are directed to computer systems configured to perform the steps of any of the methods described herein, potentially with different components performing a respective step or a respective group of steps. Although presented as numbered steps, steps of methods herein can be performed at a same time or in a different order. Additionally, portions of these steps may be used with portions of other steps from other methods. Also, all or portions of a step may be optional. Any of the steps of any of the methods can be performed with modules, circuits, or other means for performing these steps.

Any of the computer systems mentioned herein may utilize any suitable number of subsystems. In some embodiments, a computer system includes a single computer apparatus, where the subsystems can be the components of the computer apparatus. In other embodiments, a computer system can include multiple computer apparatuses, each being a subsystem, with internal components. The subsystems can be interconnected via a system bus. Additional subsystems include, for examples, a printer, keyboard, storage device(s), monitor, which is coupled to display adapter, and others. Peripherals and input/output (I/O) devices, which couple to I/O controller, can be connected to the computer system by any number of means known in the art, such as serial port. For example, serial port or external interface (e.g. Ethernet, Wi-Fi, etc.) can be used to connect computer system to a wide area network such as the Internet, a mouse input device, or a scanner. The interconnection via system bus allows the central processor to communicate with each subsystem and to control the execution of instructions from system memory or the storage device(s) (e.g., a fixed disk, such as a hard drive or optical disk), as well as the exchange of information between subsystems. The system memory and/or the storage device(s) may embody a computer readable medium. Any of the data mentioned herein can be output from one component to another component and can be output to the user.

A computer system can include a plurality of the same components or subsystems, e.g., connected together by external interface or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present disclosure can be implemented in the form of control logic using hardware (e.g., an application specific integrated circuit or field programmable gate array) and/or using computer software with a generally programmable processor in a modular or integrated manner. As used herein, a processor includes a multi-core processor on a same integrated chip, or multiple processing units on a single circuit board or networked. Based on the disclosure and teachings provided herein, a person of ordinary skill in the art will know and appreciate other ways and/or methods to implement embodiments of the present disclosure using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Kits an Microarrays

In another aspect, the present disclosure provides kits for use in the methods described above. The kits may comprise any or all of the reagents to perform the methods described herein. In such applications the kits may include any or all of the following: assay reagents, buffers, nucleic acids that bind to at least one of the genes described herein, hybridization probes and/or primers, antibodies or other moieties that specifically bind to at least one of the polypeptides encoded by the genes described herein, etc. In addition, the kit may include reagents such as nucleic acids, hybridization probes, primers, antibodies and the like that specifically bind to a reference gene or a reference polypeptide.

The term "kit" as used herein in the context of detection reagents, are intended to refer to such things as combinations of multiple gene expression product detection reagents, or one or more gene expression product detection reagents in combination with one or more other types of elements or components (e.g., other types of biochemical reagents, containers, packages such as packaging intended for commercial sale, substrates to which gene expression detection product reagents are attached, electronic hardware components, etc.).

In some embodiments, the present disclosure provides oligonucleotide probes attached to a solid support, such as an array slide or chip, e.g., as described in Eds., Bowtell and Sambrook *DNA Microarrays: A Molecular Cloning Manual* (2003) Cold Spring Harbor Laboratory Press. Construction of such devices are well known in the art, for example as described in US Patents and Patent Publications U.S. Pat. No. 5,837,832; PCT application WO95/11995; U.S. Pat. Nos. 5,807,522; 7,157,229, 7,083,975, 6,444,175, 6,375,903, 6,315,958, 6,295,153, and 5,143,854, 2007/0037274, 2007/0140906, 2004/0126757, 2004/0110212, 2004/0110211, 2003/0143550, 2003/0003032, and 2002/0041420. Nucleic acid arrays are also reviewed in the following references: *Biotechnol Annu Rev* (2002) 8:85-101; Sosnowski et al. *Psychiatr Genet* (2002)12(4): 181-92; Heller, *Annu Rev Biomed Eng* (2002) 4: 129-53; Kolchinsky et al., *Hum. Mutat* (2002) 19(4):343-60; and McGail et al., *Adv Biochem Eng Biotechnol* (2002) 77:21-42.

A microarray can be composed of a large number of unique, single-stranded polynucleotides, usually either synthetic antisense polynucleotides or fragments of cDNAs, fixed to a solid support. Typical polynucleotides are preferably about 6-60 nucleotides in length, more preferably about 15-30 nucleotides in length, and most preferably about 18-25 nucleotides in length. For certain types of arrays or other detection kits/systems, it may be preferable to use oligonucleotides that are only about 7-20 nucleotides in length. In other types of arrays, such as arrays used in conjunction with chemiluminescent detection technology, preferred probe lengths can be, for example, about 15-80 nucleotides in length, preferably about 50-70 nucleotides in length, more preferably about 55-65 nucleotides in length, and most preferably about 60 nucleotides in length.

In addition, the kits may include instructional materials containing directions (i.e., protocols) for the practice of the methods provided herein. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

The following examples are provided to better illustrate the claimed invention and are not to be interpreted as limiting the scope of the invention. All specific compositions, materials, and methods described below, in whole or in part, fall within the scope of the present invention. These specific compositions, materials, and methods are not intended to limit the invention, but merely to illustrate specific embodiments falling within the scope of the invention. One skilled in the art may develop equivalent compositions, materials, and methods without the exercise of inventive capacity and without departing from the scope of the invention. It will be understood that many variations can be made in the procedures herein described while still remaining within the bounds of the present invention. It is the intention of the inventors that such variations are included within the scope of the invention.

EXAMPLE 1

This example shows the identification of biomarkers for predicting response to cetuximab in patient-derived xenograft (PDX) models.

Materials and Methods

A cohort of 26 PDX models in gastric cancers were used in this study. Those models were subject to cetuximab treatment for at least two weeks. Both tumor growth inhibition (TGI) and median AUC (area under curve) ratio, a newly developed metric to evaluate drug efficacy, were calculated (Table 1). Those models can be divided into two categories according to TGI and median AUC ratio. Six models responded to cetuximab treatment (AUC<0.5 and TGI>0.8) and 20 models did not respond to cetuximab treatment (AUC>0.5 and TGI<0.6).

The genome wide gene expression level in the grafts were measured using RNA-seq. The genes with low expression levels or small variation of expression levels are removed. Then the normalized expression levels are used as the input for feature selection and modeling process.

Based on correlation of gene expression level and drug response, four genes were selected to build a model for the purpose of predicting response of cetuximab treatment. The modeling protocol included the following steps: 26 PDX models were randomly divided into training dataset and test dataset by 80%: 20% proportion; the training dataset was used for model building, while model tuning and model selection were based on 10 fold cross-validation, repeated 5 times performance metric; the test dataset was used to evaluate model performance.

We repeated the aforementioned modeling protocol for 10 times to get a robust estimation of the accuracy of our 4 genes predictive model.

Results

Based on the correlation between gene expression level and response to cetuximab treatment, we selected 4 genes to build a predictive model. The name of the genes and their corresponding p-values of Mann-Whitney U test are listed in table 2. Boxplots of gene expression level ($Log_2(FPKM+1)$) against drug response for each gene are showed in FIG. 1.

Figure 2:
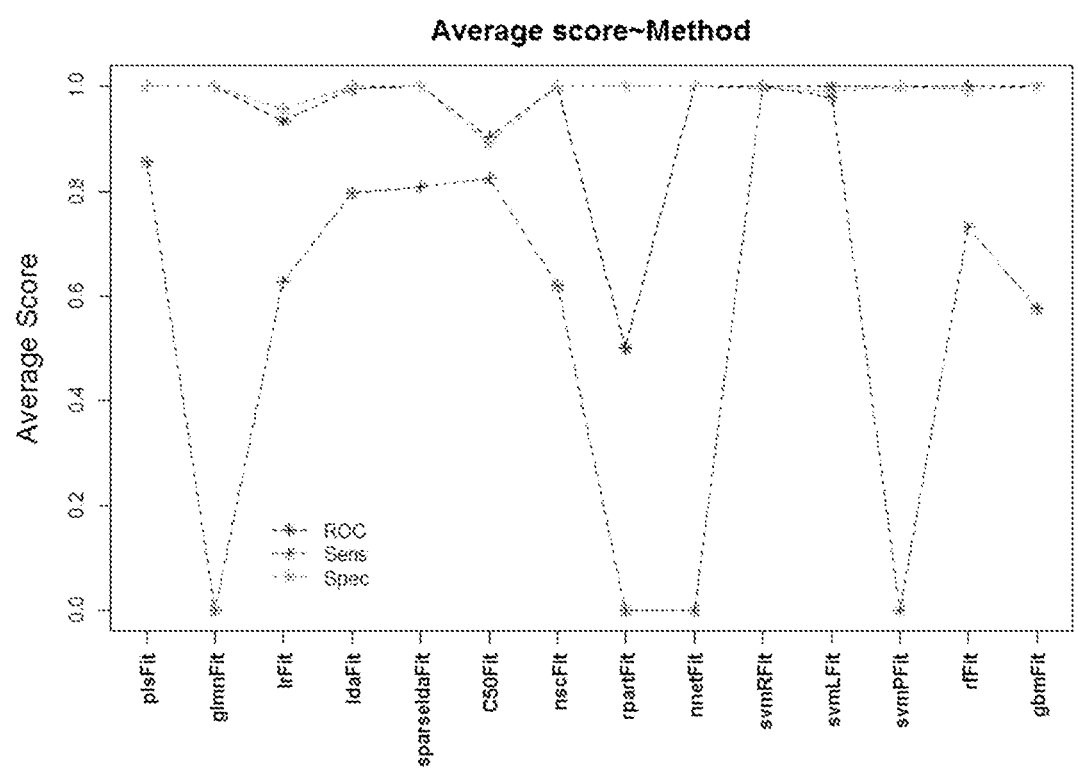
FIG. 2 shows mean ROC, sensitivity and specificity for each model using cross-validation statistic.
Figure 3:
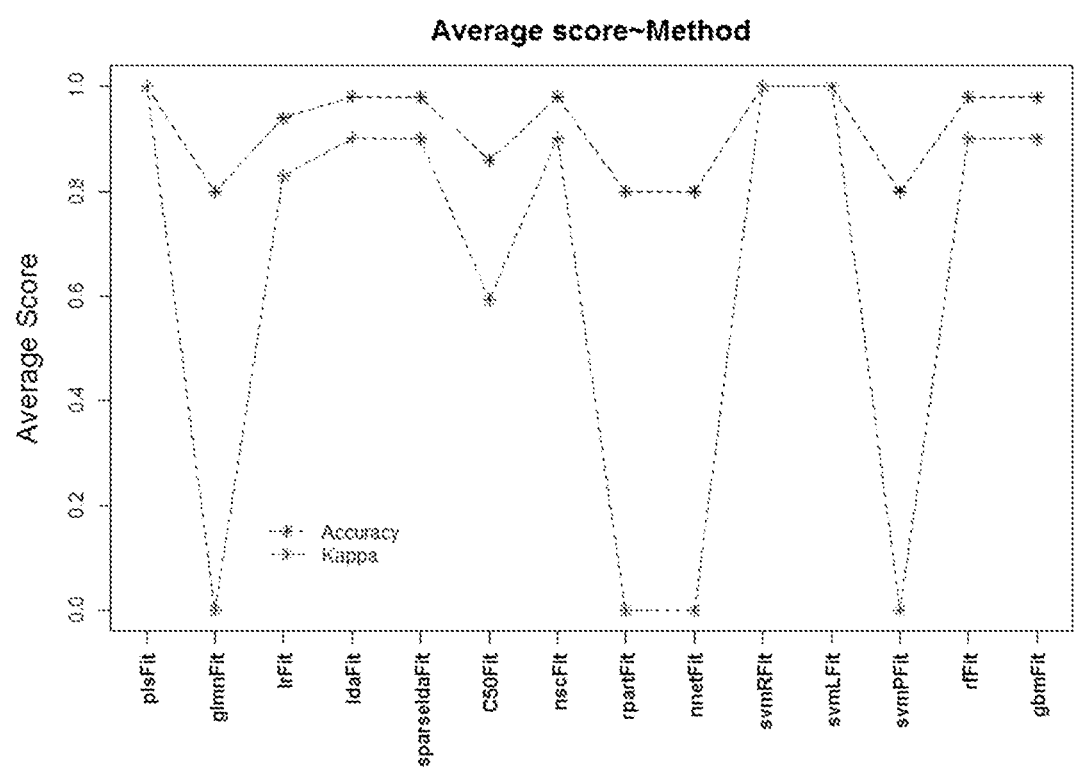
FIG. 3 shows the mean accuracy and kappa for each model based on test dataset.
Figure 4:
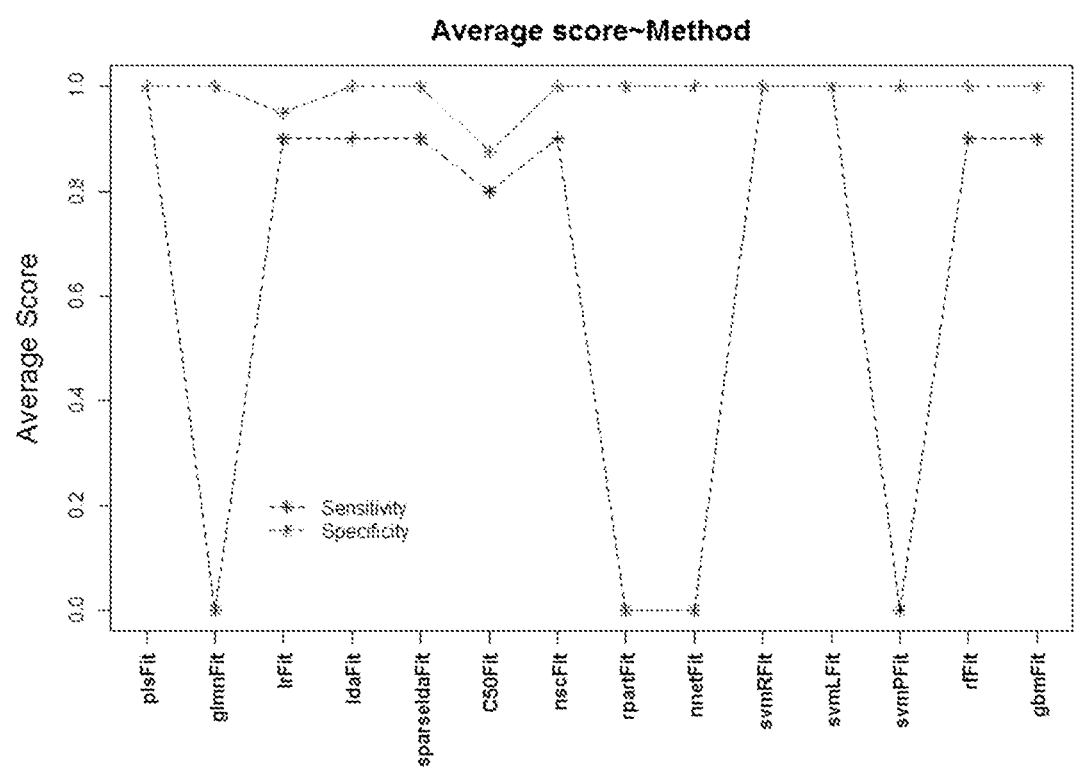
FIG. 4 shows mean sensitivity and specificity for each model based on test dataset.

Using state-of-the-art machine learning techniques such as partial least square, elastic net, support vector machine, random forest, neural net and gradient boosting machine, a total of 14 models were built based on test dataset. Judged by the average performance of 10 independent modeling runs, support vector machine (SVM) model stands out in regard of accuracy, kappa, sensitivity and selectivity. More specifically, SVM model achieved a mean accuracy of 100%, a mean sensitivity of 100% and a mean selectivity of 100% on ten independent test datasets (Table 3, FIG. 2, FIG. 3, FIG. 4).

TABLE 1

TGI, median AUC ratio of 26 PDX models

| PDX | TGI | Median AUC Ratio | Response |
|---|---|---|---|
| GA0006 | −0.420 | 1.249 | non_responder |
| GA0022 | 0.853 | −0.147 | responder |
| GA0023 | 0.074 | 0.758 | non_responder |
| GA0033 | 0.079 | 0.849 | non_responder |
| GA0037 | 0.120 | 0.870 | non_responder |
| GA0044 | 0.313 | 0.695 | non_responder |
| GA0046 | 1.011 | −0.112 | responder |
| GA0055 | 0.430 | 1.032 | non_responder |
| GA0060 | 0.512 | 0.612 | non_responder |
| GA0075 | 1.057 | −2.445 | responder |
| GA0080 | 0.167 | 0.844 | non_responder |
| GA0087 | 0.336 | 0.736 | non_responder |
| GA0098 | −0.002 | 0.684 | non_responder |
| GA0119 | 0.067 | 0.977 | non_responder |
| GA0138 | 0.101 | 0.728 | non_responder |
| GA0139 | 0.238 | 0.868 | non_responder |
| GA0151 | 0.327 | 0.807 | non_responder |
| GA0152 | 1.109 | −6.622 | responder |
| GA1224 | −1.404 | 2.120 | non_responder |
| GA2140 | −1.668 | 1.358 | non_responder |
| GA2157 | 1.106 | −0.112 | responder |
| GA3109 | 0.402 | 0.819 | non_responder |
| GA3155 | −1.014 | 1.529 | non_responder |
| GA3158 | −0.065 | 0.887 | non_responder |
| GA6203 | 1.645 | −1.133 | responder |
| GA6210 | 0.388 | 0.778 | non_responder |

TABLE 2

Symbols and Mann-Whitney U test p-value of 4 genes included in the signature

| Gene_symobl | Description | p_value |
|---|---|---|
| EGFR | Epidermal Growth Factor Receptor | 0.00541 |
| SDC2 | Syndecan 2 | 0.000934 |
| MAP6D1 | MAP6 Domain Containing 1 | 0.00951 |
| P2RY2 | Purinergic Receptor P2Y2 | 0.631 |

TABLE 3

Statistics of average performance metrics for the top models

| | | plsFit | glmnFit | lrFit | ldaFit | C50Fit | nscFit | nnetFit | svmRFit | svmLFit | rfFit | gbmFit |
|---|---|---|---|---|---|---|---|---|---|---|---|---|
| 10 fold | ROC | 1.00 | 1.00 | 0.93 | 1.00 | 0.90 | 1.00 | 1.00 | 1.00 | 1.00 | 1.00 | 1.00 |
| CV | Sens | 0.86 | 0.00 | 0.63 | 0.80 | 0.82 | 0.62 | 0.00 | 1.00 | 0.98 | 0.73 | 0.58 |
| | Spec | 1.00 | 1.00 | 0.96 | 1.00 | 0.89 | 1.00 | 1.00 | 1.00 | 0.99 | 0.99 | 1.00 |
| Test | Accuracy | 1.00 | 0.80 | 0.94 | 0.98 | 0.86 | 0.98 | 0.80 | 1.00 | 1.00 | 0.98 | 0.98 |
| dataset | Kappa | 1.00 | 0.00 | 0.83 | 0.90 | 0.59 | 0.90 | 0.00 | 1.00 | 1.00 | 0.90 | 0.90 |
| | Sensitivity | 1.00 | 0.00 | 0.90 | 0.90 | 0.80 | 0.90 | 0.00 | 1.00 | 1.00 | 0.90 | 0.90 |
| | Specificity | 1.00 | 1.00 | 0.95 | 1.00 | 0.88 | 1.00 | 1.00 | 1.00 | 1.00 | 1.00 | 1.00 |

While the disclosure has been particularly shown and described with reference to specific embodiments (some of which are preferred embodiments), it should be understood by those having skill in the art that various changes in form and detail may be made therein without departing from the spirit and scope of the present disclosure as disclosed herein.

What is claimed is:

1. A method for treating a patient having gastric cancer, the method comprising:
   administering to the patient an effective amount of cetuximab, wherein the patient has been determined as likely responsive to cetuximab by:
   measuring the levels of RNA expression of a set of biomarkers comprising EGFR, SDC2, P2RY2 and MAP6D1; and
   determining a likelihood of the patient being responsive to cetuximab based on the levels of RNA expression of the set of biomarkers.

2. The method of claim 1, wherein the levels of RNA expression are measured by an amplification assay, a hybridization assay, a sequencing assay or an array.

3. The method of claim 1, wherein the determining step is performed by a processor of a computing device.

4. The method of claim 3, wherein the determining step comprises using a machine learning model.

5. The method of claim 4, wherein the machine learning model is a support vector machine model.

* * * * *